United States Patent [19]
Edenhofer

[11] 3,951,987
[45] Apr. 20, 1976

[54] TETRAHYDROPYRIDINE DERIVATIVES

[75] Inventor: Albrecht Edenhofer, Riehen, Switzerland

[73] Assignee: Hoffmann-La Roche Inc., Nutley, N.J.

[22] Filed: Jan. 13, 1975

[21] Appl. No.: 540,753

Related U.S. Application Data

[62] Division of Ser. No. 362,636, May 21, 1973, Pat. No. 3,879,405.

[52] U.S. Cl. .............. 260/294.8 G; 260/295 AM; 260/296 R; 424/263
[51] Int. Cl.² .................................. C07D 213/32
[58] Field of Search ............. 260/294.8 G, 296 R, 260/295 AM

[56] References Cited
UNITED STATES PATENTS

| | | | |
|---|---|---|---|
| 3,674,799 | 7/1972 | Edenhofer et al. | 260/294.8 G |
| 3,706,755 | 7/1972 | Edenhofer | 260/297 R |

*Primary Examiner*—Alan L. Rotman
*Attorney, Agent, or Firm*—Samuel L. Welt; Bernard S. Leon; Frank P. Hoffman

[57] ABSTRACT

Tetrahydropyridine derivatives and processes for the preparation thereof are disclosed. These tetrahydropyridine compounds are useful as psychosedative agents.

1 Claim, No Drawings

TETRAHYDROPYRIDINE DERIVATIVES

This is a division of application Ser. No. 362,636 filed May 21, 1973 now U.S. Pat. No. 3,879,405.

DESCRIPTION OF THE INVENTION

The present invention relates to novel chemical compounds and to processes for the preparation thereof, said compounds having valuable therapeutic properties. More particularly, the present invention is concerned with new tetrahydropyridine derivatives of the general formula

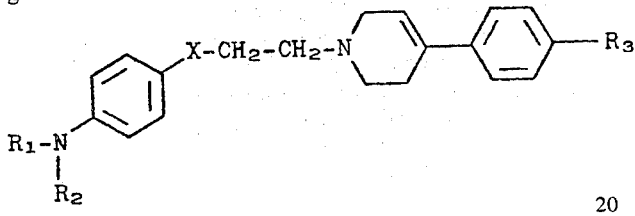

I wherein $R_1$ signifies hydrogen, lower alkyl, lower alkanoyl, lower alkyl-sulfonyl, cycloalkyl or cycloalkyl-lower alkyl; $R_2$ signifies hydrogen, lower alkyl, cycloalkyl or cycloalkyl-lower alkyl; $R_3$ signifies fluorine, chlorine or lower alkoxy; X signifies an oxygen atom or a sulfur atom and the pharmaceutically acceptable acid addition salts thereof.

As used herein, either alone or in combination such as in lower alkyl-sulfonyl, the term "lower alkyl" comprehends straight or branched chain hydrocarbon groups having from 1 to 7 carbon atoms, preferably from 1 to 4 carbon atoms, such as methyl, ethyl, propyl, isopropyl, n-hexyl and the like. The term "lower alkxoy" designates straight or branched chain saturated hydrocarbonoxy groups containing from 1 to 7 carbon atoms, preferably from 1 to 4 carbon atoms, such as methoxy, ethoxy, propoxy and the like. The term "lower alkanoyl" denotes the residue of a straight or branched chain aliphatic carboxylic acid, containing from 1 to 7 carbon atoms, for example formyl, acetyl, propionyl, isobutyryl and n-valeryl. The term "cycloalkyl" encompasses cyclic hydrocarbon groups having from 3 to 6 carbon atoms such as cyclopropyl, cyclobutyl, cyclopentyl and the like. Examples of the cycloalkyl-lower alkyl groups include cyclopropyl-methyl, cyclopropyl-ethyl and the like.

A preferred class of compounds falling within the scope of formula I are those wherein X represents an oxygen atom, i.e. compounds of the formula

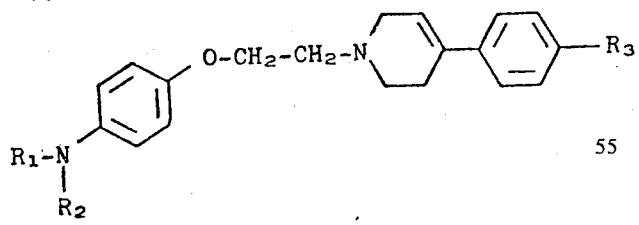

Ia wherein $R_1$-$R_3$ are as described above.

Another preferred class of compounds falling within the scope of formula I are those wherein $R_3$ signifies fluorine, i.e. compounds of the formula

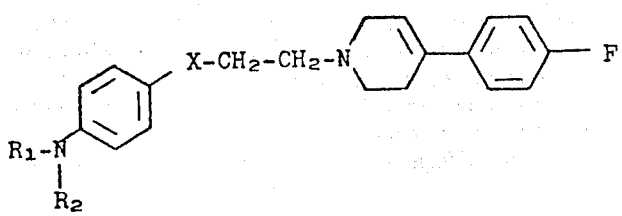

Ib wherein $R_1$, $R_2$ and X are as described above.

Particularly preferred of the compounds of formula I above are those wherein $R_1$ represents a lower alkanoyl group, preferably the acetyl group, $R_2$ represents hydrogen, $R_3$ represents fluorine and X represents oxygen. Most preferred of the compounds of formula I is: 4{2-[4-(p-fluorophenyl)-3,6-dihydro-1(2H)-pyridyl]-ethoxy}-acetanilide.

The novel compounds of formula I can be prepared following a variety of synthetic routes.

A. In one such process aspect, the compounds of formula I above can be prepared by condensing a compound of the general formula

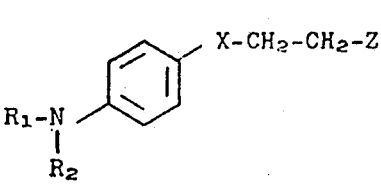

II wherein $R_1$, $R_2$ and X are as described above and Z represents a suitable leaving group
with a compound of the general formula

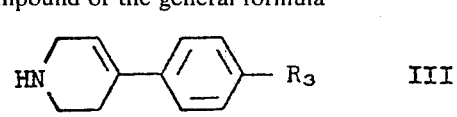

III wherein $R_3$ is as described above.

Suitable leaving groups in the starting materials of formula II above include a halogen atom, preferably chlorine or bromine, a lower alkylsulfonyloxy group, preferably mesyloxy, an arylsulfonyloxy group, preferably tosyloxy or benzene-sulfonyloxy, or the group $-N(R_4)_3^+ A^-$ in which $R_4$ signifies lower alkyl and A signifies the anion of an acid.

The condensation of a compound of formula II with a compound of formula III is expediently effected in the presence of a polar organic solvent. Suitable for this purpose are lower alkanols such as methanol, ethanol, isopropanol and the like; cyclic ethers such as tetrahydrofuran and dioxane and dimethylformamide or dimethyl sulfoxide. The condensation is advantageously effected at a temperature between room temperature and the reflux temperature of the reaction mixture. Where, in the starting material of formula II the leaving group designated as Z represents a halogen atom or a lower alkyl - or aryl-sulfonyloxy group, the condensation reaction is preferably carried out in the presence of an acid binding agent, for example in the presence of an alkali carbonate such as potassium carbonate.

The starting materials of formula II above may be prepared by reacting a compound of the formula

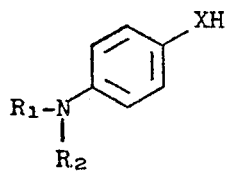

IV wherein $R_1$, $R_2$ and X are as described above with a 2-halo-ethanol of the formula

   V to yield a compound of the formula

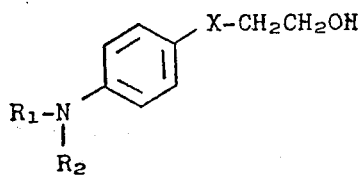

VI wherein $R_1$, $R_2$ and X are as described above.

The compound of formula VI so obtained can then be reacted with a halogenating agent, such as thionyl chloride to obtain the compound of formula II wherein Z signifies halogen. This halogenation reaction is preferably effected in the presence of an inert organic solvent such as chloroform or benzene at a temperature between about room temperature and the reflux temperature of the reaction mixture.

Alternately, the compound of formula VI above can be reacted with an alkyl- or aryl- substituted sulfonic acid halide, preferably the chloride, to yield the desired compound of formula II wherein Z signifies an alkyl- or aryl- sulfonyloxy group. This reaction is expediently effected in the presence of an acid binding agent at a temperature between about 0°C and room temperature.

The compounds of formula II above wherein Z represents the group -N($R_4$)$_3$ $^+$ A$^-$, $R_4$ and A being defined above, can be prepared by amination of the corresponding compounds of formula II wherein Z signifies halogen. This amination can be effected by reacting the halo-substituted compound of formula II with a dialkylamine, preferably dimethylamine; this reaction is expediently effected in a closed vessel at an elevated temperature, for example between about 50° and 150°C. The product obtained as a result of this amination is subsequently quaternized by reaction with an alkylating agent such as an alkyl chloride; alkyl bromide or alkylsulfate, preferably methyl chloride, methyl bromide or dimethyl sulfate. The quaternization is preferably carried out at a temperature of from about room temperature to about 75°C. Both the amination and quaternization are expediently carried out in the presence of an inert solvent such as an alkanol, i.e. methanol, or in dioxane or benzene.

The starting materials of formula II wherein X signifies oxygen and the leaving group Z is a halogen atom may also be prepared by reacting a compound of formula IV wherein X is oxygen with an excess of a 1,2-dihaloethane, preferably 1,2-dibromoethane in the presence of an excess of aqueous alkali, preferably caustic soda. This reaction is preferably carried out at a temperature between room temperature and the boiling point of the reaction mixture.

The starting materials of formula III wherein $R_3$ signifies lower alkoxy can be prepared, for example, by employing a Grignard reaction. Thus, for instance, the reaction between N-benzyl-4-piperidone and p-methoxy-phenyl magnesium bromide, followed by hydrogenolytic cleavage of the benzyl group and treatment with a dehydrating agent such as, for example, thionyl chloride or alcoholic hydrochloric acid, yields the desired compound of formula III wherein $R_3$ is methoxy.

B. In another process aspect of the present invention, the compounds of formula I above can be prepared by reacting a compound of the formula

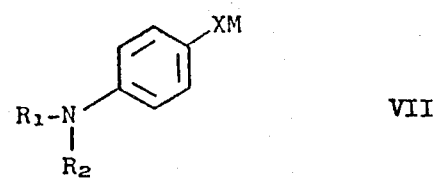

VII wherein $R_1$, $R_2$ and X are as described above and M signifies an alkali metal or a halomagnesium radical with a compound of the formula

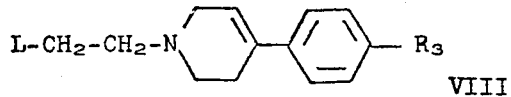

VIII wherein $R_3$ is as described above and L is a suitable leaving group.

The substituent M in the starting materials of formula VII preferably represents an alkali metal, especially sodium or potassium. In addition, M can also represent a halo-magnesium radical such as the bromo-magnesium or chloro-magnesium radical.

The leaving group in the compounds of formula VIII designated by the symbol L is preferably a halogen atom, especially chlorine or bromine, or an alkyl- or aryl-sulfonyloxy group, especially mesyloxy or tosyloxy.

The reaction between a compound of formula VII wherein M is potassium an alkali metal and a compound of formula VIII is effected in the presence of an alkali alkanolate, for example sodium ethanolate, in the corresponding alkanol, for example, ethanol. When the M substituent in the compounds of formula VII represents a halo-magnesium radical, the reaction of this formula VII compound with a compound of formula VIII is preferably carried out in a polar organic solvent such as in an ether, i.e. dimethyl ether, tetrahydrofuran or dioxane. This reaction is preferably carried out at a temperature between room temperature and the reflux temperature of the reaction mixture.

The starting materials of formula VIII are expediently prepared by reacting a compound of formula III above with a 2-halo-ethanol, preferably 2-chloro-ethanol, to yield a compound of the formula

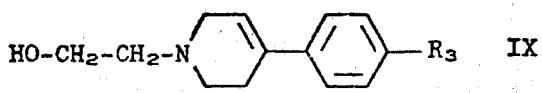

wherein $R_3$ is as described above.

This reaction is preferably effected in polar solvent such as, for example, an alkanol, i.e. methanol, ethanol and the like, dimethylformamide or dimethyl sulfoxide. It is preferable to carry out this reaction in the presence of an acid binding agent, for example, in the presence of an alkali carbonate such as potassium carbonate and at a temperature between room temperature and the reflux temperature of the reaction medium.

The compound of formula IX thus obtained can subsequently be reacted with a halogenating agent such as thienyl chloride to yield the desired starting material of formula VIII in which L represents a halogen atom. This halogenation is preferably effected in the presence of an inert solvent, for example benzene or chloroform, at a temperature between room temperature and the reflux temperature of the reaction mixture.

The compound of formula IX above can alternatively be reacted with an alkyl- or aryl- substitued sulfonic acid halide, preferably the chloride, to give the desired starting material of formula VIII in which L represents an alkyl- or aryl- substituted sulfonyloxy group. This reaction is expediently effected in the presence of an acid binding agent, for example, pyridine or triethylamine, at a temperature between about 0°C and room temperature.

C. In a further process aspect of the present invention, the desired compounds of formula I above can be prepared by dehydrating a compound of the formula

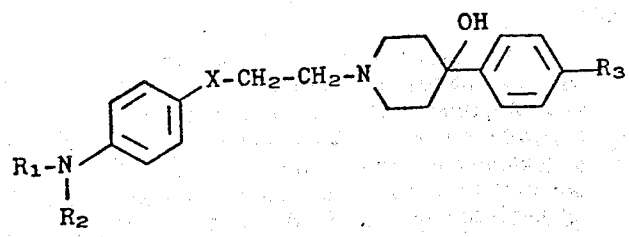

wherein $R_1$, $R_2$, $R_3$ and X are as described above.

The dehydration of the compounds of formula X above is effected employing conventional techniques, as for example by treating said compound with a standard dehydrating agent. Suitable dehydrating agents for this purpose include acetic acid anhydride, acetyl chloride, thionyl chloride, p-toluenesulfonic acid, sulfuric acid, aluminum oxide, calcium chloride and the like. This dehydration reaction is expediently effected in an inert organic solvent such as chloroform, toluene, or glacial acetic acid and at a temperature between room temperature and the reflux temperature of the reaction mixture.

The starting materials of formula X can, for example, be prepared by reacting a compound of formula II above with an appropriately substituted 4-hydroxy-4-phenyl-piperidine. This reaction is preferably effected in a polar solvent such as an alkanol, i.e. methanol, ethanol and the like, dimethylformamide, dimethyl sulfoxide or tetrahydrofuran and in the presence of an acid binding agent such as an alkali carbonate, preferably potassium carbonate. The temperature range for this reaction is preferably between room temperature and the reflux temperature of the reaction medium.

D. In another process aspect of this invention, the desired compounds of formula I above can be prepared by treating a compound of the general formula

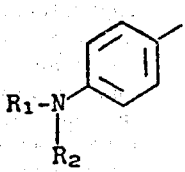

wherein $R_1$, $R_2$, $R_3$ and X are as described above with a mineral acid.

The treatment of the starting material formula XI with a mineral acid is preferably carried out using concentrated hydrochloric acid. In so doing, the acid treatment of the formula XI compound is effected at a temperature between about 0°C and the reflux temperature of the reaction mixture, preferably at an elevated temperature, for a prolonged period, for example between three to 6 hours. It should be noted that any lower alkanoyl group present in the starting material of formula XI as the $R_1$ substituent will be saponified under these reaction conditions.

The starting materials of formula XI above can, for example, be prepared by reacting a compound of formula II above with an appropriately substituted 6-methyl-6-phenyl-tetrahydro-1,3-oxazine. This reaction is preferably effected in a polar solvent such as an alkanol, i.e. methanol, ethanol and the like, dimethylformamide, dimethyl sulfoxide or tetrahydrofuran and in the presence of an acid binding agent such as, for example, an alkali carbonate, preferably potassium carbonate. This reaction is expediently carried out at a temperature between room temperature and the reflux temperature of the reaction mixture.

E. In a further process aspect of this invention, the compounds of formula I above wherein $R_1$ and $R_2$ each signify hydrogen can be prepared by reducing a compound of the general formula

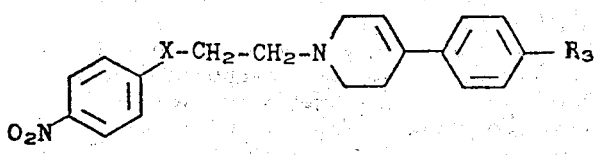

XII wherein $R_3$ and X are as described above.

The reduction of the starting material of formula XII is preferably carried out by treatment of said compound with hydrazine in the presence of a noble metal catalyst such as palladium on charcoal or platinum oxide. Alternatively, the reduction can also be carried out by treatment of the formula XII compound with sodium dithionite or with nascent hydrogen which can be provided, for example, by using a mineral acid such as hydrochloric acid and a metal which is capable of liberating hydrogen such as zinc or iron. This reduction is expediently conducted in the presence of a lower alkanol, preferably ethanol, or in a cyclic ether, preferably tetrahydrofuran. The reduction is preferably carried out at a temperature between room temperature and the reflux temperature of the reaction mixture.

The starting materials of formula XII can be prepared, for example, by condensing a 4-nitro-1-(2-haloethoxy or 2-haloethylthio)-benzene with a compound of formula III above. The conditions employed for the condensation of the appropriately substituted benzene compound with the formula III compound are essentially the same as those described in process aspect A above for the condensation of compounds of formulae II and III.

F. In another process aspect of the instant invention, a compound of the general formula

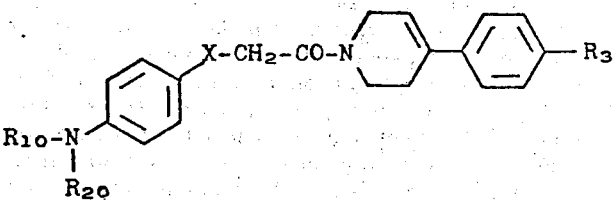

XIII wherein $R_3$ and X are as described above; $R_{10}$ signifies hydrogen, lower alkyl, lower alkanoyl, cycloalkyl or cycloalkyl-lower alkyl; $R_{20}$ signifies hydrogen, lower alkyl, cycloalkyl or cycloalkyl-lower alkyl; or $R_{10}$ and $R_{20}$ together each represent an oxygen atom is reduced to yield a compound of the formula

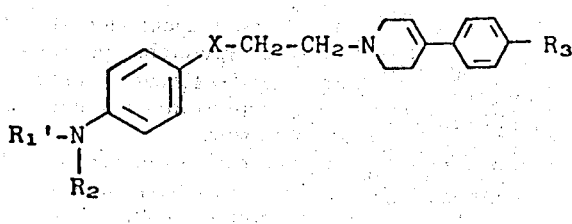

Ic wherein $R_2$, $R_3$ and X are as described above and $R_1'$ signifies hydrogen, lower alkyl, lower alkanoyl, cycloalkyl or cycloalkyl-lower alkyl.

The starting material of formula XIII is reduced by treatment of said compound with a complex metal hydride, preferably lithium aluminum hydride. This reduction is preferably effected in an organic solvent such as ether, tetrahydrofuran, dioxane or diglyme, and at a temperature between about 0°C and the reflux temperature of the reaction mixture. If, in the starting materials of formula XIII, $R_{10}$ and $R_{20}$ each signify an oxygen atom, the nitro group present in the starting material is first reduced following the procedures set forth in process aspect E above, and then the acid amide function is reduced as described above.

The starting materials of formula XIII can, for example, be prepared by reacting a compound of the general formula

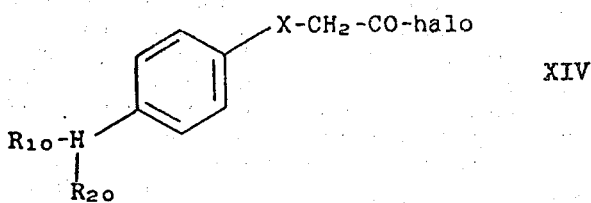

XIV wherein $R_{10}$, $R_{20}$ and X are as described above with a compound of formula III above. The halogen leaving group in the compounds of formula XIV is preferably chlorine. This reaction is expediently effected in the presence of an inert organic solvent such as benzene or chloroform and in the presence of an acid-binding agent, preferably a tertiary organic base such as triethylamine or pyridine. The reaction is preferably carried out at a temperature between 0°C. and the reflux temperature of the reaction mixture.

G. The compounds of formula I above wherein $R_1$ signifies lower alkyl, lower alkanoyl, lower alkylsulfonyl, cycloalkyl or cycloalkyl-lower alkyl can be prepared following conventional techniques by introducing the desired $R_1$ substituent into the corresponding compound of the formula I wherein $R_1$ signifies hydrogen, i.e., into a compound of the formula

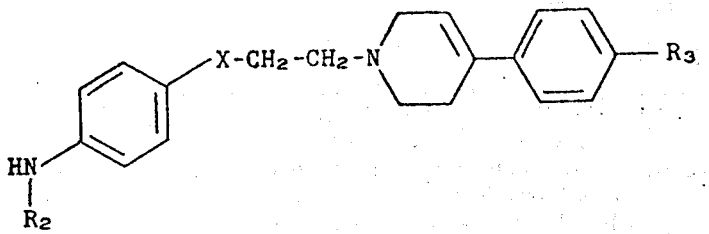

Id wherein $R_2$, $R_3$ and X are as described above.

The introduction of the desired $R_1$ substituent into the compound of formula Id above can be affected following conventional alkylating, alkanoylating or alkylsulfonylating techniques. Thus, for example, a lower alkyl, cycloalkyl or cycloalkyl-lower alkyl group can be introduced using standard alkylating procedures as by reacting the formula Id compound with an appropriate alkylating agent such as methyl iodide, cyclopropyl-bromide, dimethyl sulfate and the like. In a further example, the compound of formula Id can be treated with an appropriate acid halide or acid anhydride such as acetyl chloride, acetic anhydride, cyclopropane carboxylic acid chloride or methane sulfonic acid chloride to yield the correspondingly substituted compound of formula I. The treatment with an acid chloride is preferably effected in the presence of an acid-binding agent, for example, a tertiary organic base such as triethylamine or pyridine, and and inert organic solvent such as benzene, chloroform, tetrahydrofuran or dimethyl sulfoxide and at a temperature between room temperature and the reflux temperature of the reaction medium. The treatment with an acid anhydride is preferably effected in a polar protonic solvent such as an alkanol, for example methanol, or in the presence of a dilute alkanecarboxylic acid, for example, dilute acetic acid. This reaction is expediently carried out at a temperature between about 0°C. and about 50°C., preferably at room temperature.

This process aspect represents a preferred procedure for the preparation of the compounds of formula I above wherein $R_1$ signifies a lower alkyl-sulfonyl group. It is also the preferred procedure for introducing a lower alkylsulfonyl group, when desired, into the starting materials of formulae II, VII, X and XI above wherein $R_1$ signifies hydrogen.

The compounds of formula I above wherein $R_1$ signifies a lower alkanol group can be saponified following conventional techniques, as for example, by treating said compound with dilute aqueous caustic alkali or with aqueous acid. It is advantageous to use about 20 percent hydrochloric acid at an elevated temperature, especially at the reflux temperature of the reaction mixture.

The compounds of formula I above are basic and thus form acid addition salts with both pharmaceutically acceptable organic or inorganic acids, for example, with hydrohalic acids such as hydrochloric acid, hydrobromic acid and hydroiodic acid, with other mineral acids such as sulfuric acid, phosphoric acid and nitric acid, as well as with organic acids such as tartaric acid, citric acid, oxalic acid, camphorsulfonic acid, ethanesulfonic acid, toluenesulfonic acid, salicylic acid, ascorbic acid, maleic acid, mandelic acid and the like. Preferred salts are the hydrohalides, especially the hydrochlorides. The acid addition salts are preferably manufactured in a suitable solvent such as ethanol or acetonitrile by treatment of the free base with the corresponding non-aqueous acid.

The compounds of formula I above are, in part, crystalline substances which are relatively readily soluble in dimethyl sulphoxide, dimethylformamide, in chlorinated hydrocarbons such as, for example, chloroform or methylene chloride and in alkanols such as methanol or ethanol, but which are relatively insoluble in water.

The acid addition salts of the compounds of formula I are crystalline substances. They are readily soluble in dimethyl sulphoxide, dimethylformamide, in alkanols such as methanol or ethanol and, usually, also in water. They are relatively insoluble in benzene, petroleum ether and in chlorinated hydrocarbons such as, for example, chloroform or methylene chloride.

As indicated above, the compounds of formula I above exhibit psychosedative activity. The psychosedative activity of the tetrahydropyridine derivatives of formula I is demonstrated in warm blooded animals using the standard "open field" test with rats [Psychopharmacologia I, 389–392 (1960)]. The dosage which caused a 50 percent decrease (in comparison to the untreated controls) in the number of diameter crossings is expressed as the $ED_{50}$. The results of the test for representative compounds of formula I are shown in the following Table:

TABLE 1

| Tetrahydropyridine derivative | $ED_{50}$ mg/kg p.o. | Toxicity (mouse) mg/kg p.o. |
|---|---|---|
| 4'-[2-[4-(p-fluoro-phenyl)-3,6-dihydro-1(2H)-pyridyl]-ethoxy]-acetanilide | 0.6 | 250–500 |
| 4'-[2-[4-(p-fluoro-phenyl)-3,6-dihydro-1(2H)-pyridyl]-ethoxy]-propionanilide | 0.6 | 150–300 |
| p-[2-[4-(p-fluoro-phenyl)-3,6-dihydro-1(2H)-pyridyl]-ethoxy]-aniline | 0.6 | 250–500 |

The tetrahydropyridine derivatives provided by this invention can be used as medicaments; for example, in the form of pharmaceutical preparations which contain them in association with a compatible pharmaceutical carrier. This carrier can be an organic or inorganic inert carrier material which is suitable for enteral or parenteral application such as, for example, gelatin, gum arabic, lactose, starches, magnesium stearate, talc, vegetable oils, polyalkylene glycols etc. The pharmaceutical preparations are preferably made up in solid form (e.g., as tablets, dragees, suppositories or capsules). They can also contain yet other therapeutically valuable substances.

Expedient pharmaceutical dosage forms contain about 5–100 mg. of a compound of formula I. Expedient oral dosage ranges lie at about 0.1 mg/kg/day to about 10 mg/kg/day. However, the stated ranges can be extended upwards or downwards depending on the individual requirement of the patient or the directions given by the specialist.

The starting materials of formulae X, XI, XII, and XIII are novel and as such form a part of the present invention. The following examples further illustrate the scope of the noted invention. Unless otherwise indicated, the temperature stated are in degrees centigrade.

EXAMPLE 1

21.4 g. of 4-(p-fluorophenyl)-1,2,3,6-tetrahydropyridine hydrochloride, 25.8 g. of 4'-(2-bromoethoxy)acetanilide, 30 g. of potassium carbonate and a few crystals of potassium iodide are heated under reflux conditions in 200 ml. of ethanol and 20 ml. of water for 24 hours. While still hot, the mixture is decanted from the aqueous phase, 100 ml. of water are added and the mixture is allowed to cool, with crude 4'-{2-[4-(p-fluorophenyl)-3,6-dihydro-1(2H)-pyridyl]ethoxy}acetanilide crystallizing out of solution. This is dissolved in a mixture of 150 ml. of methanol and 50 ml. of acetic acid ethyl ester and converted by addition of alcoholic hydrochloric acid, until the mixture becomes acidic, into the hydrochloride, which crystallizes after the addition of 100 ml. of acetic acid ethyl ester. The hydrochloride melts at 214°–216°C. (dec.).

Following similar procedures to those set forth above, the following compounds may also be prepared:

a. 4'-{2-[4-(p-fluorophenyl)-3,6-dihydro-1(2H)pyridyl]ethoxy}propionanilide hydrochloride, m.p. 244°–246°C. (from methanol-acetic acid ethyl ester) from 4'-(2-bromoethoxy)-propionanilide and 4-(p-fluorophenyl)-1,2,3,6-tetrahydropyridine;

b. 4'-{2-[4-(p-chlorophenyl)-3,6-dihydro-1(2H)pyridyl]ethoxy}isobutyranilide hydrochloride, m.p. 239°–246°C. (from methanol-acetic acid ethyl ester) from 4'-(2-bromoethoxy)-isobutyranilide and 4-(p-chlorophenyl)-1,2,3,6-tetrahydropyridine c. 4'-{2-[4-(p-fluorophenyl)-3,6-dihydro-1(2H)pyridyl]ethoxy}-isobutyranilide hydrochloride, m.p. 239°–241°C. (from methanol-acetic acid ethyl ester) from 4'-(2-bromoethoxy)-isobutyranilide and 4-(p-fluorophenyl)-1,2,3,6-tetrahydropyridine;

d. 4'-{2-[4-(p-chlorophenyl)-3,6-dihydro-1(2H)pyridyl]ethoxy}acetanilide hydrochloride, m.p. 228°–229°C. (from methanol-acetic acid ethyl ester) from 4-(2-bromoethoxy)-acetanilide and 4-(p-chlorophenyl)-1,2,3,6-tetrahydropyridine;

e. 4'-{2-[4-(p-methoxyphenyl)-3,6-dihydro-1(2H)-pyridyl]ethoxy}acetanilide, m.p. 163°–164°C. (from methanol) from 4'-(2-bromoethoxy)acetanilide and 4-(p-methoxyphenyl)-1,2,3,6-tetrahydropyridine.

The 4'-(2-bromoethoxy)propionanilide employed as a starting material can be manufactured as follows:

82.5 g. of p-propionamidophenol are introduced into a solution of 20 g. of sodium hydroxide in 20 ml. of water and 400 ml. of ethanol and, with strong stirring, treated with 470 g. of 1,2-dibromoethane. The mixture is heated under reflux conditions for 3 hours and the dibromoethane is driven off with the aid of steam. The crude 4'-(2-bromoethoxy)propionanilide which precipitates is washed with water and recrystallized from ethanol with the addition of water. The compound melts at 151°C.

The 4'-(2-bromoethoxy)isobutyranilide employed as starting material can be manufactured in a manner analogous to that described above, m.p. 143°C. (from ethanol).

EXAMPLE 2

1.8 G. of 4'-[(2-chloroethyl)thio]acetanilide, 2.7 g. of 4-(p-fluorophenyl)-1,2,3,6-tetrahydropyridine, 4.5 g. of potassium carbonate and a few crystals of potassium iodide are heated under reflux conditions in 50 ml. of ethanol and 5 ml. of water for 16 hours. The solvent is evaporated under reduced pressure, the residue is taken up in chloroform and washed with water. From the organic phase there is obtained crude 4'-{[2-[4-(p-fluorophenyl)-3,6-dihydro-1(2H)-pyridyl]-ethyl]thio}acetanilide which melts at 150°–152°C. after recrystallization from acetic acid ethyl ester.

The 4'-[(2-chloroethyl)thio]-acetanilide employed as starting material can be manufactured as follows:

A solution of 17.5 g. of 4'-[(2-hydroxyethyl)thio]-acetanilide in 500 ml. of absolute benzene is treated dropwise with stirring with 17.5 g. of thionyl chloride and heated under reflux conditions for 1 hour. The crude 4'-[(2-chloroethyl)-thio]-acetanilide remaining behind after evaporation of the solvent under reduced pressure melts at 153°–155°C. after repeated crystallization from acetic acid ethyl ester. A further crystallization can be obtained from the mother liquor by adsorption on silica gel and elution with methylene chloride.

EXAMPLE 3

7.8 G. of 4'-{2-[4-(p-fluorophenyl)-3,6-dihydro-1(2H)-pyridyl]-ethoxy}acetanilide and 40 ml. of about 20% hydrochloric acid are heated under reflux conditions for 1 hour. The crude p-{2-[4-(p-fluorophenyl)-3,6-dihydro-1(2H)-pyridyl]ethoxy}aniline dihydrochloride hydrate which precipitates on cooling melts at 180°–183°C. after recrystallization from ethanol-acetic acid ethyl ester-diethyl ether.

EXAMPLE 4

0.8 G. of p-{2-[4-(p-fluorophenyl)-3,6-dihydro-1(2H)-pyridyl]ethoxy}aniline are dissolved in 10 ml. of 3-N acetic acid and treated with 0.5 g. of acetic acid anhydride. The solution is stored at room temperature for 12 hours and subsequently evaporated under reduced pressure. The residue is taken up in chloroform, this extract washed with 1-N caustic soda and evaporated. The residual crude 4'-{2-[4-(p-fluorophenyl)-3,6-dihydro-1(2H)-pyridyl]ethoxy}acetanilide melts at 139°C. after recrystallization from acetic acid ethyl ester.

EXAMPLE 5

A solution of 4.5 g. of p-{2-[4-(p-fluorophenyl)-3,6-dihydro-1(2H)-pyridyl]ethoxy}aniline in 15 ml. of chloroform is treated with 2 g. of triethylamine. A solution of 1.7 g. of methanesulfonic acid chloride in 10 ml. of chloroform is added thereto with stirring and cooling at a temperature range of 0°–10°C. The reaction mixture is allowed to stand at room temperature for 20 hours. It is washed with water and the solvent is evaporated. The residual crude 4'-{2-[4-(p-fluorophenyl)-3,6-dihydro-1(2H)-pyridyl]ethoxy}-methanesulfonanilide melts at 137°–139°C. after recrystallization from methanol.

EXAMPLE 6

0.1 G. of 4'-{2-[4-(p-fluorophenyl)-4-hydroxypiperidino]ethoxy}acetanilide are dissolved in 30 ml. of chloroform with slight heating and 0.2 g. of thionyl chloride are added. The mixture is heated under reflux conditions for 4 hours. The crude 4'-{2-[4(p-fluorophenyl)-3,6-dihydro-1(2H)-pyridyl]ethoxy}acetanilide hydrochloride remaining after evaporation of the solvent melts at 213°–215°C. (dec.) after recrystallization from methanol-diethyl ether.

The 4'-{2-[4-(p-fluorophenyl)-4-hydroxypiperidino]ethoxy acetanilide employed as starting material can be manufactured as follows:

1.3 G. of 4-(p-fluorophenyl)-4-hydroxypiperidine, 1.5 g. of 4'-(2-bromoethoxy)-acetanilide, 1 g. of potassium carbonate and a few crystals of potassium iodide are heated under reflux conditions in 20 ml. of isopropanol for 24 hours. The residue remaining after evaporation of the solvent is taken up in chloroform and washed with water. The crude 4'-{2-[4-(p-fluorophenyl)-4-hydroxypiperidino]-ethoxy}acetanilide obtainable from the organic phase melts at 174°–175°C. after recrystallization twice from isopropanol.

EXAMPLE 7

0.2 G. of 4'-{2-[6-(p-fluorophenyl)-dihydro-6-methyl-2H-1,3-oxazin-3(4H)-yl]ethoxy}acetanilide hydrochloride and 2 ml. of conc. hydrochloric acid are heated on the steam bath for 4 hours. The excess hydrochloric acid is evaporated under reduced pressure and the residue brought to crystallization with ethanol-acetic acid ethyl ester. The p-{2-[4-(p-fluorophenyl)-3,6-dihydro-1(2H)-pyridyl]ethoxy}aniline dihydrochloride hydrate obtained melts at 180°–183°C. after recrystallization from ethanol-acetic acid ethyl ester.

The 4'-{2-[6-(p-fluorophenyl)-dihydro-6-methyl-2H-1,3-oxazin-3(4H)-yl]-ethoxy}-acetanilide employed as starting material can be manufactured as follows:

5.2 G. of 4'-(2-bromoethoxy)acetanilide, 4 g. of 6-methyl-6-(p-fluorophenyl)-tetrahydro-1,3-oxazine, 5 g. of potassium carbonate and a few crystals of potassium iodide are heated under reflux conditions in 50 ml. of ethanol for 16 hours. After evaporation of the solvent under reduced pressure, the residue is dissolved in chloroform and washed with water. The crude product obtained from the organic phase is absorbed on silica gel and purified by elution with methylene chloride-ether (1:1). There is obtained an oil which is converted into the hydrochloride as previously described. The pure 4'-{2-[6-(p-fluorophenyl)-dihydro-6methyl-2H-1,3-oxazin-3(4H)-yl]ethoxy}acetanilide melts at 180°C. (dec.) after recrystallization from acetic acid ethyl ester.

EXAMPLE 8

A solution of 0.3 g. of 1-[(p-aminophenoxy)acetyl]-4-(p-fluorophenyl)-1,2,3,6-tetrahydropyridine in 5 ml. of absolute tetrahydrofuran is added dropwise at room temperature with stirring and nitrogen gassing to a suspension of 0.3 g. of lithium aluminum hydride in 10 ml. of absolute tetrahydrofuran. The stirring is continued at room temperature for 16 hours and water is cautiously added, initially dropwise. After filtration, the mixture is extracted with chloroform. The oily residue is purified by column chromatography on silica gel with diethyl ether-acetic acid ethyl ester (1:1) as eluting agent and converted into the hydrochloride as previously described. The p-2-[4-(p-fluorophenyl)-3,6-dihydro-1(2H)-pyridyl]-ethoxy aniline dihydrochloride hydrate melts at 180°–183°C. after crystallization with ethanol-acetic acid ethyl ester-ether.

The 1-[(p-aminophenoxy)-acetyl]-4-(p-fluorophenyl)-1,2,3,6-tetrahydropyridine employed as starting material can be manufactured as follows:

A solution of 4.3 g. of p-nitrophenoxyacetic acid chloride in 10 ml. of absolute benzene is added dropwise with stirring and cooling to a solution of 3.6 g. of p-fluorophenyl-1,2,3,6-tetrahydropyridine and 5 g. of triethylamine in 20 ml. of absolute benzene and the reaction mixture is heated under reflux conditions for 1 hour. After cooling, the triethylamine hydrochloride thereby precipitated is extracted with water and the organic phase is washed with 1N hydrochloric acid and water. The crude 4-(p-fluorophenyl)-1,2,3,6-tetrahydro-1-[(p-nitrophenoxy)acetyl]pyridine obtained after evaporation of the solvent melts at 134°–136°C. after recrystallization from isopropanol.

2.3 g. of this compound and 2.5 g. of hydrazine hydrate are dissolved in 50 ml. of absolute tetrahydrofuran. 0.2 g. of platinum dioxide are added portionwise commencing the strong evolution of nitrogen. After cessation of the evolution of gas, the mixture is heated under reflux conditions for 15 hours and subsequently filtered. After evaporation of the solvent, the residue is purified by column chromatography on silica gel with methylene chloride as eluting agent. The 1-[(p-aminophenoxy)acetyl]-4-(p-fluorophenyl)-1,2,3,6-tetrahydropyridine obtained from the eluate melts at 120°–122°C. after recrystallization from benzene.

EXAMPLE 9

0.3 g. of p-acetamidophenol are dissolved in a solution of 0.12 g. of sodium in 10 ml. of absolute ethanol and 0.55 g. of 1-(2-chloroethyl)-4-(p-fluorophenyl)-1,2,3,6-tetrahydropyridine hydrochloride are added thereto all at once. The reaction mixture is heated under reflux conditions for 24 hours, filtered from the precipitated sodium chloride and the filtrate evaporated to dryness. The residue is absorbed on silica gel and eluted with methylene chloride-ether (1:1). The 4'-{2-[4-(p-fluorophenyl)-3,6-dihydro-1(2H)-pyridyl]-ethoxy}-acetanilide obtained from the eluate melts at 139°C. after recrystallization from acetic acid ethyl ester.

The 1-(2-chloroethyl)-4-(p-fluorophenyl)-1,2,3,6-tetrahydropyridine employed as starting material can be manufactured as follows:

1.77 g of 4-(p-fluorophenyl)-1,2,3,6-tetrahydropyridine, 0.8 g. of ethylene chlorohydrin, 1.2 g. of sodium carbonate and a few crystals of sodium iodide are heated under reflux conditions in 10 ml. of ethanol for 24 hours and filtered hot and the filtrate is evaporated to dryness. The residual oil is purified by column chromatography on silica gel with acetic acid ethyl ester-ethanol (1:1) as eluting agent. The 1-(2-hydroxyethyl)-4-(p-fluorophenyl)-1,2,3,6-tetrahydropyridine obtained from the eluate melts at 96°–98°C. after recrystallization from cyclohexane.

0.5 g. of 1-(2-hydroxyethyl)-4-(p-fluorophenyl)-1,2,3,6-tetrahydropyridine are dissolved in 10 ml. of absolute benzene and 0.4 g. of thionyl chloride are added with stirring and cooling with ice. The mixture is heated under reflux conditions for 30 minutes and the solvent is evaporated. The 1-(2-chloroethyl)-4-(p-fluorophenyl)-1,2,3,6-tetrahydropyridine hydrochloride obtained melts at 226°C. after recrystallization from ethanol.

EXAMPLE 10

0.2 g. of powdered iron is added to a solution of 0.34 g. of 4-(p-fluorophenyl)-1,2,3,6-tetrahydro-1-[2-(p-nitrophenoxy) ethyl]pyridine in a mixture of 2 ml. of 1N hydrochloric acid, 10 ml. of ethanol and 10 ml. of water. The mixture is refluxed for 4 hrs., cooled and made alkaline by addition of 1N sodium hydroxide. After addition of 20 ml. of chloroform and celite, the mixture is filtered. The organic phase is separated, dried and evaporated. The oily residue obtained is dissolved in ethyl acetate and converted to the hydrochloride by addition of ethanolic hydrogen chloride. The 1-[2-(p-aminophenoxy)ethyl]-4-(p-fluorophenyl)-1,2,3,6-tetrahydropyridine dihydrochloride obtained in this way has m.p. 180°–181° after recrystallization from ethanol/ethylacetate/ether.

The starting material may be prepared as follows:

A mixture of 2.15 g. of 4-(p-fluorophenyl)-1,2,3,6-tetrahydropyridine hydrochloride, 2.5 g. of p-(2-bromoethoxy)-nitrobenzene, 2.8 g. of potassium carbonate, 20 ml. of ethanol and 2 ml. of water is refluxed for 3 days. After filtration the crude product crystallizes from the hot reaction mixture. It is purified by chromatography on silica gel using methylene chloride for elution. The 4-(p-fluorophenyl)-1,2,3,6-tetrahydro-1-[2-(p-nitrophenoxy)ethyl]pyridine obtained melts at 104°–107° after recrystallization from ethanol.

EXAMPLE 11

Manufacture of capsules of the following composition:

4'-{2-[4(p-fluorophenyl)-4,6-dihydro-1(2H)-pyridyl]ethoxy}acetanilide

| | |
|---|---|
| hydrochloride | 10 mg. |
| Mannitol | 110 mg. |
| Talcum | 5 mg. |
| | 125 mg. |

The active substance is homogeneously mixed with the talcum and mannitol, passed through a No. 5 sieve (mesh width about 0.23 mm) and again thoroughly mixed. The mixture obtained is filled into No. 4 gelatin capsules.

EXAMPLE 12

Manufacture of dragees of the following composition:

4'-{2-[4-(p-fluorophenyl)-3,6-dihydro-1(2H)-pyridyl]ethoxy}acetanilide

| | |
|---|---|
| hydrochloride | 25 mg. |
| Mannitol | 100 mg. |
| Corn starch | 20 mg. |
| Talcum | 5 mg. |
| | 150 mg. |

The active substance is mixed with the mannitol and passed through a No. 5 sieve (mesh width about 0.23 mm). A 10% aqueous paste is prepared from the corn starch and homogeneously mixed with the mannitol-active substance mixture. The slightly moist mash is passed through a No. 2 sieve (mesh width about 1.0 mm). The granulate obtained is dried and, after the addition of the talcum, pressed to biconvex cores with a weight of 150 mg. The cores are coated with a sugar layer in the usual manner by dredging.

I claim:
1. A compound of the formula

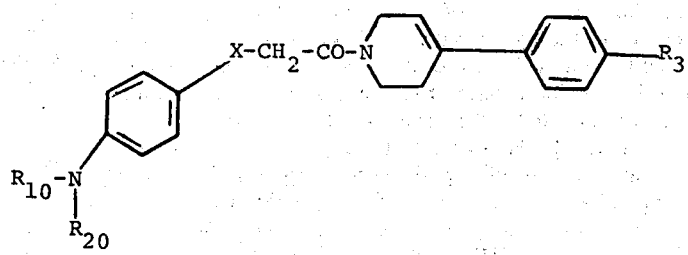

wherein $R_3$ signifies fluorine, chlorine or lower alkoxy; X signifies an oxygen atom or a sulfur atom; $R_{10}$ signifies hydrogen, lower alkyl, lower alkanoyl, $C_3$ to $C_6$ cycloalkyl or $C_3$ to $C_6$ cycloalkyl-lower alkyl; $R_{20}$ signifies hydrogen, lower alkyl, $C_3$ to $C_6$ cycloalkyl or $C_3$ to $C_6$ cycloalkyl-lower alkyl; or $R_{10}$ and $R_{20}$ each represent an oxygen atom and together with the nitrogen atom represent nitro.

* * * * *